US010274618B2

(12) United States Patent
Nakamura (10) Patent No.: US 10,274,618 B2
(45) Date of Patent: Apr. 30, 2019

(54) RADIOGRAPHY APPARATUS, RADIOGRAPHY METHOD, AND RADIOGRAPHY PROGRAM

(71) Applicant: FUJIFILM CORPORATION, Minato-ku, Tokyo (JP)

(72) Inventor: Kenji Nakamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/792,775

(22) Filed: Oct. 25, 2017

(65) Prior Publication Data
US 2018/0120458 A1 May 3, 2018

(30) Foreign Application Priority Data
Nov. 2, 2016 (JP) ................ 2016-215098

(51) Int. Cl.
| | | |
|---|---|---|
| *G01T 1/29* | (2006.01) | |
| *G01D 18/00* | (2006.01) | |
| *G01T 1/20* | (2006.01) | |
| *H01L 27/148* | (2006.01) | |
| *H04N 5/32* | (2006.01) | |
| *H04N 5/353* | (2011.01) | |
| *A61B 6/00* | (2006.01) | |

(52) U.S. Cl.
CPC ......... *G01T 1/2928* (2013.01); *G01D 18/006* (2013.01); *G01T 1/20* (2013.01); *H01L 27/14856* (2013.01); *H04N 5/32* (2013.01); *H04N 5/353* (2013.01); *A61B 6/4208* (2013.01); *A61B 6/462* (2013.01)

(58) Field of Classification Search
CPC .... A61B 6/4208; A61B 6/462; G01D 18/006; G01T 1/20; G01T 1/2928; H01L 27/14856; H04N 5/32; H04N 5/353
See application file for complete search history.

(56) References Cited

U.S. PATENT DOCUMENTS

| | | | | |
|---|---|---|---|---|
| 2008/0237479 A1* | 10/2008 | Iwakiri | ............... | G01T 1/2928 250/370.08 |
| 2010/0327176 A1* | 12/2010 | Takenaka | ............... | H04N 5/335 250/394 |

(Continued)

FOREIGN PATENT DOCUMENTS

JP 2005-026796 A1 1/2005

*Primary Examiner* — Mark R Gaworecki
(74) *Attorney, Agent, or Firm* — SOLARIS Intellectual Property Group, PLLC (57) ABSTRACT

A radiography apparatus includes: a radiation detector that includes a plurality of pixels, each of which includes a thin film transistor and which are two-dimensionally arranged, and data lines through which charge accumulated in the connected pixels is transmitted as an electric signal; and a first sample-and-hold unit and a second sample-and-hold unit that sample and hold the electric signal transmitted through the data line. In a case in which the charge accumulated in the pixel is read out, the radiography apparatus performs control such that the thin film transistor is turned off and the first sample-and-hold unit samples and holds a first electric signal transmitted through the data line; and the thin film transistor is turned on and the second sample-and-hold unit samples and holds a second electric signal transmitted through the data line.

12 Claims, 9 Drawing Sheets

(56) References Cited

U.S. PATENT DOCUMENTS

| | | | | |
|---|---|---|---|---|
| 2011/0134289 A1* | 6/2011 | Mochizuki | ............... | H04N 5/32 348/246 |
| 2012/0008177 A1* | 1/2012 | Fujimura | ............... | H04N 5/357 358/482 |
| 2013/0342514 A1* | 12/2013 | Yokoyama | ............. | G09G 5/003 345/204 |
| 2014/0139713 A1* | 5/2014 | Gomi | ................ | H01L 27/14618 348/308 |
| 2014/0185764 A1* | 7/2014 | Takenaka | ................. | A61B 6/42 378/62 |
| 2015/0279882 A1* | 10/2015 | Yagi | .................. | H01L 27/14609 348/301 |
| 2016/0270755 A1* | 9/2016 | Takenaka | .................. | G01T 1/20 |

* cited by examiner

RADIOGRAPHY APPARATUS, RADIOGRAPHY METHOD, AND RADIOGRAPHY PROGRAM

CROSS-REFERENCE TO RELATED APPLICATION

This application claims priority under 35 USC 119 from Japanese Patent Application No. 2016-215098 filed on Nov. 2, 2016, the disclosure of which is incorporated by reference herein.

BACKGROUND OF THE INVENTION

1. Field of the Invention

The present disclosure relates to a radiography apparatus, a radiography method, and a radiography program.

2. Description of the Related Art

In recent years, a technique has been known which changes the time when an electric signal obtained by performing photoelectric conversion for an optical image of an object is sampled and held in an imaging apparatus using a charge coupled device (CCD) sensor (see JP2005-026796A).

SUMMARY OF THE INVENTION

However, in the capture of a radiographic image by a radiation detector provided with pixels including switching elements, such as thin film transistors (TFTs), in many cases, before and after a control signal is input to the switching element, an electric signal that is transmitted through a data line connected to the pixels is sampled and held.

In this case, the difference between the electric signals sampled and held before and after the control signal for turning on the switching element is input to a gate electrode of the switching element is used as an output signal from the pixel to generate image data.

In a case in which the switching element is changed from an on state to off state and in a case in which the switching element is changed from the off state to the on state, charge is moved from a parasitic capacitance between the gate electrode and the source electrode of the switching element. Therefore, after the switching element is turned on to read out the charge accumulated in the pixel, the switching element is turned off and the radiography apparatus waits until charge is moved from the parasitic capacitance. Then, the radiography apparatus samples and holds the electric signal. As a result, there is a problem that it is difficult to reduce the time required to capture a radiographic image.

The technique disclosed in JP2005-026796A uses the CCD sensor. Therefore, the period for which the radiography apparatus waits for the movement of charge from the parasitic capacitance is negligible. For this reason, the technique disclosed in JP2005-026796A does not consider the problem.

The present disclosure has been made in view of the above-mentioned problems and an object of the present disclosure is to provide a radiography apparatus, a radiography method, and a radiography program that can reduce the time required to capture a radiographic image.

In order to achieve the object, according to an aspect of the present disclosure, there is provided a radiography apparatus comprising: a radiation detector including a plurality of pixels, each of which includes a conversion element that generates a larger amount of charge as an amount of radiation emitted becomes larger and a switching element that is turned on and off according to a state of a control signal to read out charge generated by the conversion element and which are two-dimensionally arranged, and data lines which are connected to the pixels and through which the charge accumulated in the connected pixels is transmitted as an electric signal; a first sample-and-hold unit and a second sample-and-hold unit that sample and hold the electric signal transmitted through the data line; and a control unit that, in a case in which the charge accumulated in the pixels is read out, performs control such that the switching element is turned off and the first sample-and-hold unit samples and holds a first electric signal transmitted through the data line; and the switching element is turned on and the second sample-and-hold unit samples and holds a second electric signal transmitted through the data line.

In the radiography apparatus according to the aspect of the present disclosure, the control unit may acquire, as a correction value, a difference between the first electric signal and the second electric signal which are obtained in advance by the control performed when the radiation is not emitted before a radiographic image is captured and may correct the difference between the first electric signal and the second electric signal obtained by the control in a case in which the charge accumulated in the pixels is read out, using the correction value.

In the radiography apparatus according to the aspect of the present disclosure, the control unit may acquire, as a correction value, a difference between the first electric signal and the second electric signal which are obtained in advance by the control performed when the radiation is not emitted each time a radiographic image is captured and may correct the difference between the first electric signal and the second electric signal obtained by the control in a case in which the charge accumulated in the pixels is read out, using the correction value.

In the radiography apparatus according to the aspect of the present disclosure, the control unit may acquire the correction value before the radiation is emitted each time the radiographic image is captured.

In the radiography apparatus according to the aspect of the present disclosure, the control unit may acquire the correction value for each pixel and use the correction value for the correction.

In the radiography apparatus according to the aspect of the present disclosure, in a case in which the charge accumulated in the pixel is read out, the control unit may input, to the switching element, the control signal with a voltage value equal to a voltage value of the control signal which is input to the switching element in a case in which the correction value is acquired.

In the radiography apparatus according to the aspect of the present disclosure, the control unit may perform the control in a case in which the charge accumulated in the pixel is read out and in a case in which fluoroscopy is performed.

In the radiography apparatus according to the aspect of the present disclosure, the fluoroscopy may be fluoroscopy in a state in which radiation is emitted in a pulse shape.

In the radiography apparatus according to the aspect of the present disclosure, a first imaging mode in which the control unit performs the control and a second imaging mode in which the control unit turns off the switching element and directs the first sample-and-hold unit to sample and hold the first electric signal transmitted through the data line; and the control unit turns on the switching element, turns off the switching element, and directs the second sample-and-hold unit to sample and hold the second electric signal transmitted through the data line may be switchable.

In the radiography apparatus according to the aspect of the present disclosure, the switching element may include amorphous silicon.

In order to achieve the object, according to another aspect of the present disclosure, there is provided a radiography method that is performed by a radiography apparatus comprising a radiation detector including a plurality of pixels, each of which includes a conversion element that generates a larger amount of charge as an amount of radiation emitted becomes larger and a switching element that is turned on and off according to a state of a control signal to read out charge generated by the conversion element and which are two-dimensionally arranged, and data lines which are connected to the pixels and through which the charge accumulated in the connected pixels is transmitted as an electric signal and a first sample-and-hold unit and a second sample-and-hold unit that sample and hold the electric signal transmitted through the data line. The radiography method comprises a process of, in a case in which the charge accumulated in the pixels is read out, performing control such that the switching element is turned off and the first sample-and-hold unit samples and holds a first electric signal transmitted through the data line; and the switching element is turned on and the second sample-and-hold unit samples and holds a second electric signal transmitted through the data line.

In order to achieve the object, according to still another aspect of the present disclosure, there is provided a radiography program that causes a computer controlling a radiography apparatus comprising a radiation detector including a plurality of pixels, each of which includes a conversion element that generates a larger amount of charge as an amount of radiation emitted becomes larger and a switching element that is turned on and off according to a state of a control signal to read out charge generated by the conversion element and which are two-dimensionally arranged, and data lines which are connected to the pixels and through which the charge accumulated in the connected pixels is transmitted as an electric signal and a first sample-and-hold unit and a second sample-and-hold unit that sample and hold the electric signal transmitted through the data line to perform a process comprising: in a case in which the charge accumulated in the pixels is read out, performing control such that the switching element is turned off and the first sample-and-hold unit samples and holds a first electric signal transmitted through the data line; and the switching element is turned on and the second sample-and-hold unit samples and holds a second electric signal transmitted through the data line.

According to the present disclosure, it is possible to reduce the time required to capture a radiographic image.

DESCRIPTION OF THE PREFERRED EMBODIMENTS

Hereinafter, an embodiment of the invention will be described in detail with reference to the drawings.

Figure 1:
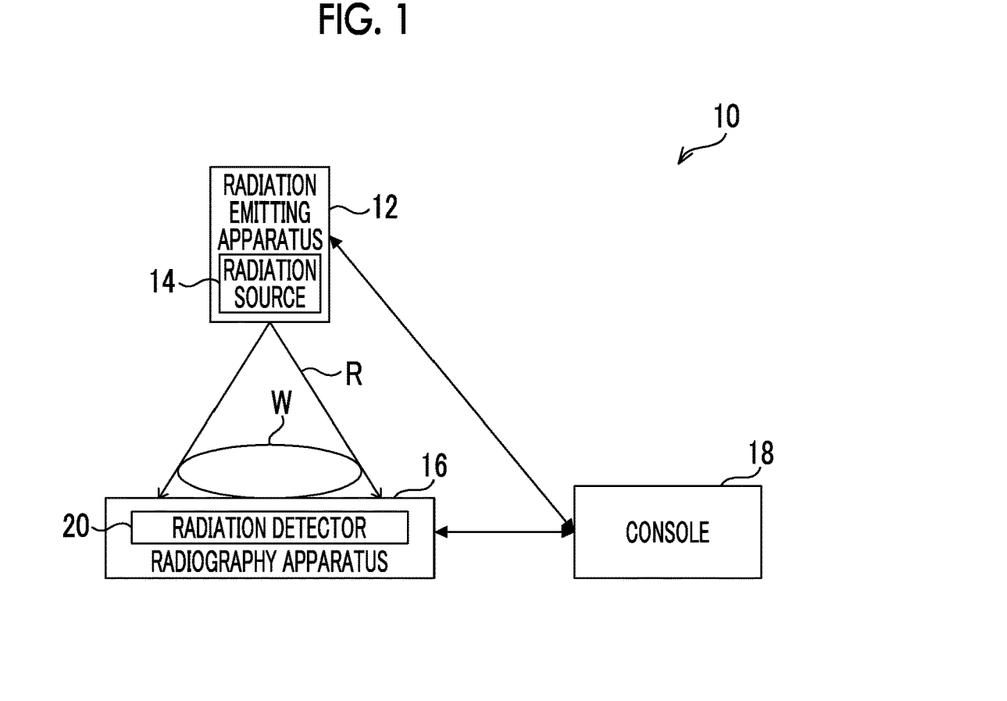
FIG. 1 is a block diagram illustrating an example of the configuration of a radiography system according to an embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for instructing the radiation emitting apparatus 12 to emit the radiation R is not particularly limited. For example, in a case in which the radiation emitting apparatus 12 includes an irradiation button, a user, such as a radiology technician, may press the irradiation button to instruct the emission of the radiation R such that the radiation R is emitted from the radiation emitting apparatus 12. In addition, for example, the user, such as a radiology technician, may operate the console 18 to instruct the emission of the radiation R such that the radiation R is emitted from the radiation emitting apparatus 12.

When receiving a command to emit the radiation R, the radiation emitting apparatus 12 emits the radiation R from the radiation source 14 according to set irradiation conditions, such as a tube voltage, a tube current, and an irradiation period. Hereinafter, the dose of the radiation R is simply referred to as "the amount of radiation".

The radiography apparatus 16 according to this embodiment includes a radiation detector 20 that detects the radiation R which has been emitted from the radiation emitting apparatus 12 and then transmitted through the subject W. The radiography apparatus 16 captures a radiographic image of the subject W using the radiation detector 20.

Figure 2:
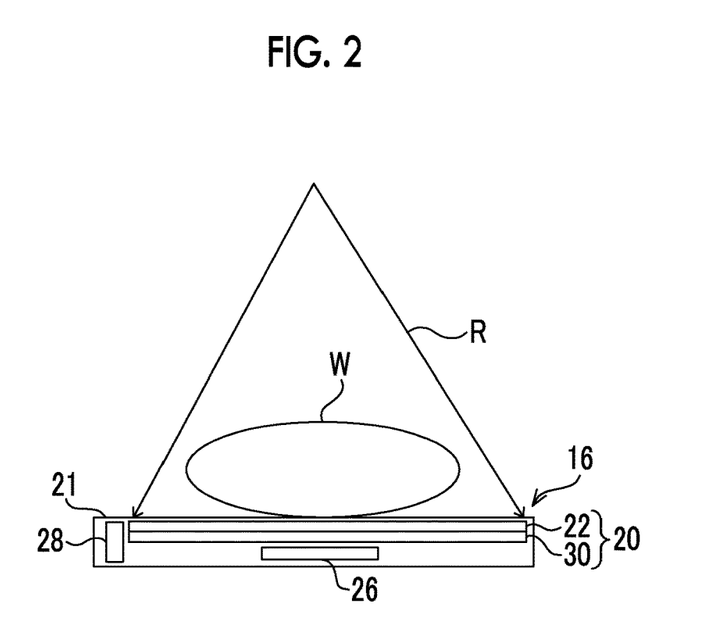
FIG. 2 is a side cross-sectional view illustrating an example of the configuration of a radiography apparatus according to the embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes the radiation detector 20, a control substrate 26, and a case 28.

The radiation detector 20 includes a scintillator 22 which is an example of a light emitting layer that is irradiated with the radiation R and emits light and a thin film transistor (TFT) substrate 30. The scintillator 22 and the TFT substrate 30 are stacked in the order of the scintillator 22 and the TFT substrate 30 from the incident side of the radiation R.

That is, the radiation detector 20 is a so-called penetration side sampling (PSS) radiation detector on which the radiation R is incident from the scintillator 22.

The control substrate 26 is provided so as to correspond to the radiation detector 20 and electronic circuits, such as an image memory 56 and a control unit 58 which will be described below, are formed on the control substrate 26. In addition, the control substrate 26 is provided on the side of the second radiation detector 20 which is opposite to the incident side of the radiation R.

The case 28 is provided at a position (that is, outside the range of an imaging region) that does not overlap the radiation detector 20 at one end of the housing 21. For example, a power supply unit 70 which will be described below, is accommodated in the case 28. The installation position of the case 28 is not particularly limited. For example, the case 28 may be provided at a position that overlaps the radiation detector 20 on the side of the radiation detector 20 which is opposite to the incident side of the radiation R.

Next, the configuration of a main part of an electrical system of the radiography apparatus 16 according to this embodiment will be described with reference to FIG. 3.

Figure 3:
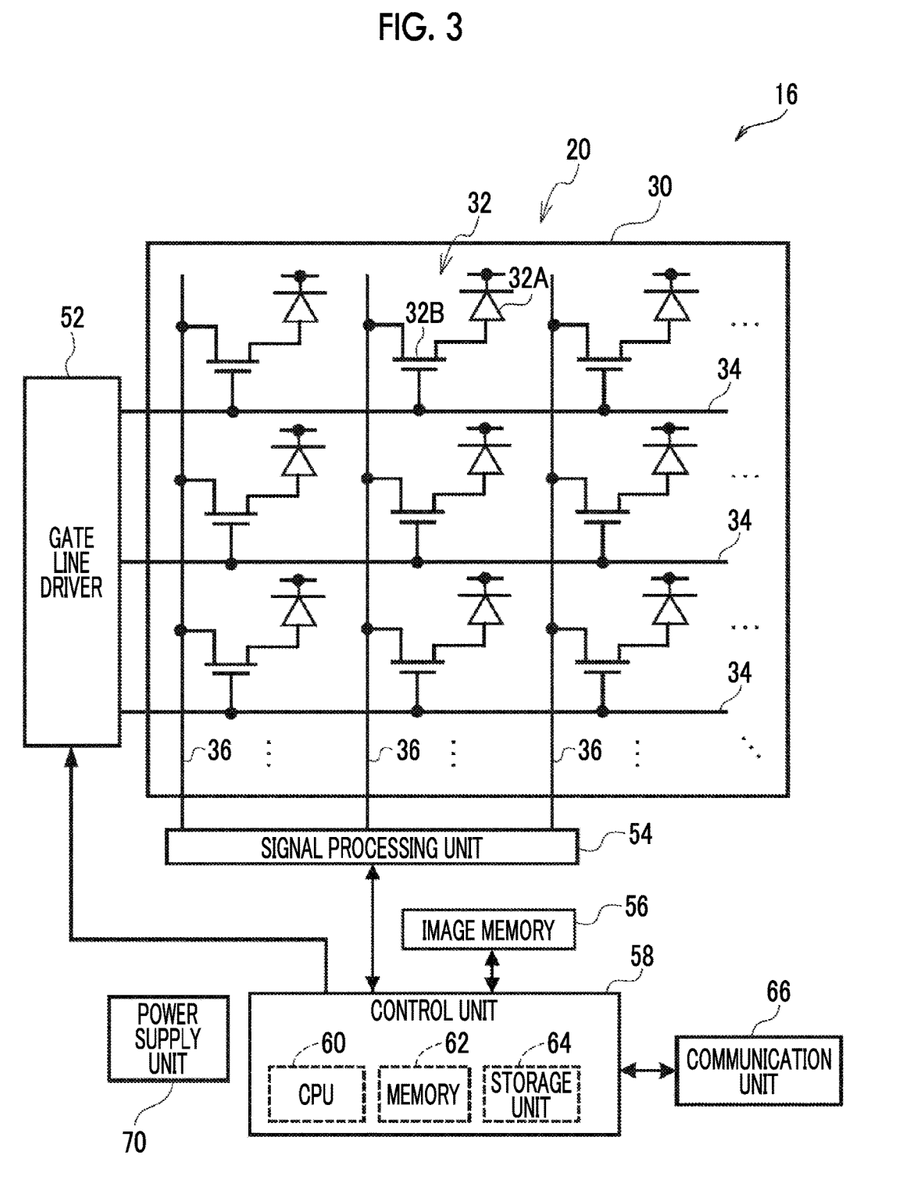
FIG. 3 is a block diagram illustrating an example of the configuration of a main part of an electrical system of the radiography apparatus according to the embodiment.

As illustrated in FIG. 3, a plurality of pixels 32 are two-dimensionally provided in one direction (a row direction in FIG. 3) and an intersection direction (a column direction in FIG. 3) that intersects the one direction in the TFT substrate 30. The pixel 32 includes a sensor unit 32A and a thin film field effect transistor (TFT; hereinafter, simply referred to as a "thin film transistor") 32B.

The sensor unit 32A includes, for example, an upper electrode, a lower electrode, and a photoelectric conversion film which are not illustrated, absorbs light emitted from the scintillator 22, generates charge, and accumulates the generated charge. The thin film transistor 32B converts the charge accumulated in the sensor unit 32A into an electric signal and outputs the electric signal. The sensor unit 32A is an example of a conversion element which generates a larger amount of charge as the amount of radiation becomes larger.

The thin film transistor 32B according to this embodiment includes amorphous silicon. Since the detailed configuration of the thin film transistor 32B is disclosed in, for example, JP2014-022851A and JP2014-220841A, the description thereof will not be repeated here.

A plurality of gate lines 34 which extend in the one direction and are used to turn on and off each thin film transistor 32B are provided in the TFT substrate 30. In addition, a plurality of data lines 36 which extend in the intersection direction and are used to read out charge through the thin film transistors 32B in an on state are provided in the TFT substrate 30.

A gate line driver 52 is provided on one side of two adjacent sides of the TFT substrate 30 and a signal processing unit 54 is provided on the other side. Each gate line 34 of the TFT substrate 30 is connected to the gate line driver 52 and each data line 36 of the TFT substrate 30 is connected to the signal processing unit 54.

Each row of the thin film transistors 32B of the TFT substrate 30 is sequentially turned on by an electric signal (hereinafter, also referred to as a control signal) which is supplied from the gate line driver 52 through the gate lines 34. The charge read out by the thin film transistor 32B in an on state is transmitted as an electric signal through the data line 36 and is input to the signal processing unit 54. In this way, charge is sequentially read out from each row of the thin film transistors and image data indicating a two-dimensional radiographic image is acquired.

Figure 4:
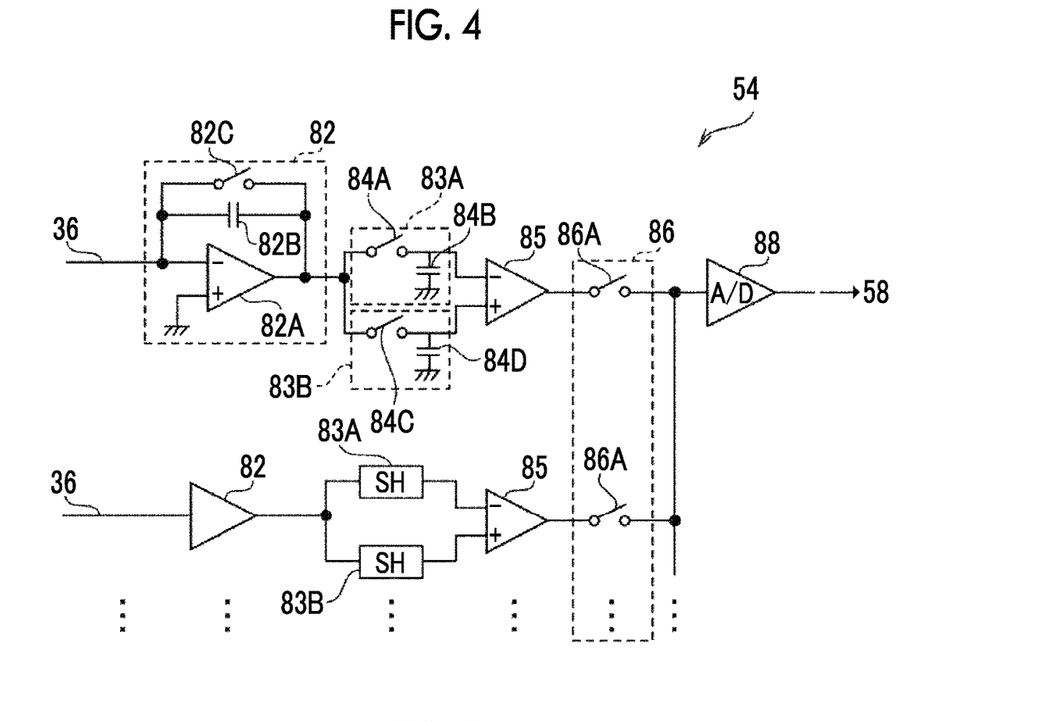
FIG. 4 is a circuit diagram illustrating an example of the configuration of a signal processing unit according to the embodiment.

For example, as illustrated in FIG. 4, the signal processing unit 54 includes charge amplifiers 82 and sample-and-hold circuits 83A as an example of first sample-and-hold units which correspond to each data line 36. In addition, the signal processing unit 54 includes sample-and-hold circuits 83B as an example of second sample-and-hold units and operational amplifiers 85 which correspond to each data line 36. The control unit 58 is connected to the signal processing unit 54.

The charge amplifier 82 includes an operational amplifier 82A having a positive input side connected to the ground, and a capacitor 82B and a reset switch 82C which are connected in parallel to each other between a negative input side and an output side of the operational amplifier 82A. The reset switch 82C is turned on and off by the control unit 58.

The sample-and-hold circuit 83A includes a switch 84A and a capacitor 84B. The sample-and-hold circuit 83B includes a switch 84C and a capacitor 84D. The operational amplifier 85 has a negative input side that is connected to the output side of the sample-and-hold circuit 83A and a positive input side that is connected to the output side of the sample-and-hold circuit 83B. That is, the operational amplifier 85 outputs a difference signal between an output signal from the sample-and-hold circuit 83A and an output signal from the sample-and-hold circuit 83B. The switch 84A and the switch 84C are also turned on and off by the control unit 58.

The signal processing unit 54 includes a multiplexer 86 and an analog/digital (A/D) converter 88. A switch 86A provided in the multiplexer 86 is also turned on and off by the control unit 58.

In a case in which a radiographic image is detected, first, the control unit 58 keeps the reset switch 82C of the charge amplifier 82 on for a predetermined period to release the charge accumulated in the capacitor 82B.

The charge generated in the pixel 32 by the emission of the radiation R is accumulated in the sensor unit 32A and is read out to the data line 36 by the thin film transistor 32B in an on state. The charge read out to the data line 36 is transmitted as an electric signal and is amplified at a predetermined gain by a corresponding charge amplifier 82.

After discharging the capacitor 82B, the control unit 58 drives the sample-and-hold circuits 83A and 83B for a predetermined period at different times. Then, the sample-and-hold circuits 83A and 83B sample and hold the level of the electric signal amplified by the charge amplifier 82 at different times. In addition, an electric signal corresponding to the difference between the electric signals sampled and held by the sample-and-hold circuits 83A and 83B is output from the operational amplifier 85. That is, so-called correlated double sampling is performed by the sample-and-hold circuits 83A and 83B and the operational amplifier 85.

Then, the electric signals output from each operational amplifier 85 are sequentially selected by the multiplexer 86 under the control of the control unit 58 and the selected electric signals are converted into digital signals by the A/D converter 88. In this way, image data indicating a captured radiographic image is acquired.

The image data output from the A/D converter 88 of the signal processing unit 54 is sequentially output to the control unit 58. The image memory 56 is connected to the control unit 58 and the image data sequentially output from the signal processing unit 54 is sequentially stored in the image memory 56 under the control of the control unit 58. The image memory 56 has memory capacity that can store a predetermined amount of image data. Whenever a radiographic image is captured, captured image data is sequentially stored in the image memory 56.

The control unit 58 includes a central processing unit (CPU) 60, a memory 62 including, for example, a read only memory (ROM) and a random access memory (RAM), and a non-volatile storage unit 64 such as a flash memory. An example of the control unit 58 is a microcomputer.

A communication unit 66 is connected to the control unit 58 and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52, the signal processing unit 54, the image memory 56, the control unit 58, and the communication unit 66). In FIG. 3, lines for connecting the power supply unit 70 to various circuits and elements are not illustrated in order to avoid complication.

With the above-mentioned configuration, the radiography apparatus 16 according to this embodiment captures a radiographic image using the radiation detector 20.

Figure 5:
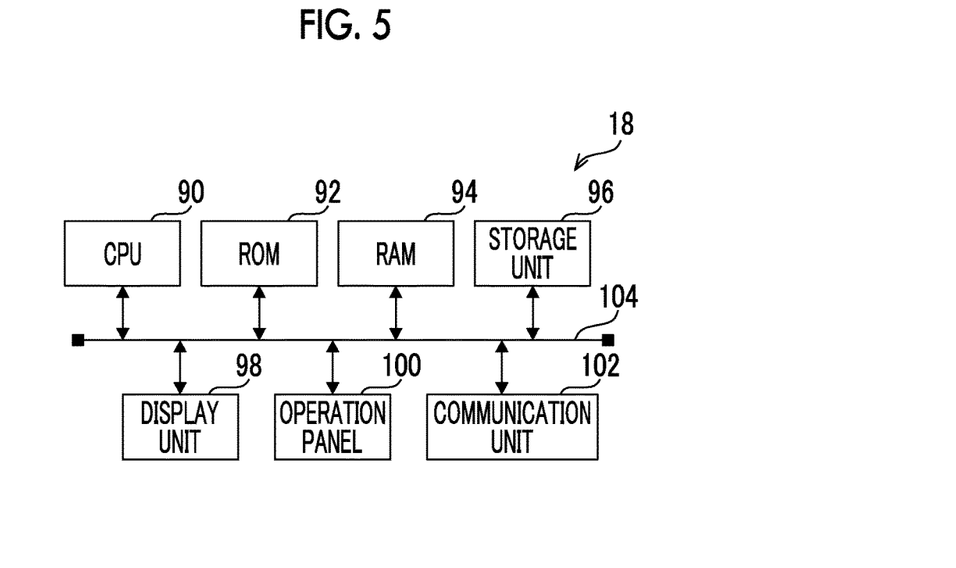
FIG. 5 is a block diagram illustrating an example of the configuration of a main part of an electrical system of a console according to the embodiment.

Next, the configuration of the console 18 according to this embodiment will be described with reference to FIG. 5. As illustrated in FIG. 5, the console 18 includes a CPU 90 that controls the overall operation of the console 18 and a ROM 92 in which, for example, various programs or various parameters are stored in advance. In addition, the console 18 includes a RAM 94 that is used as, for example, a work area when the CPU 90 executes various programs and a non-volatile storage unit 96 such as a hard disk drive (HDD).

The console 18 further includes a display unit 98 that displays, for example, an operation menu and a captured radiographic image and an operation panel 100 which includes a plurality of keys and to which various kinds of information or operation commands are input. In addition, the console 18 includes a communication unit 102 that transmits and receives various kinds of information to and from external apparatuses, such as the radiation emitting apparatus 12 and the radiography apparatus 16, using at least one of wireless communication or wired communication. The CPU 90, the ROM 92, the RAM 94, the storage unit 96, the display unit 98, the operation panel 100, and the communication unit 102 are connected to each other through a bus 104.

The radiography system 10 according to this embodiment can perform fluoroscopy (the capture of motion pictures) that emits the radiation R in a pulse shape to continuously capture radiographic images, in addition to capturing still images. Hereinafter, the period for which the radiation R is emitted to accumulate charge in the pixel 32 is referred to as an "accumulation period" and the period for which the charge accumulated in the pixel 32 for the accumulation period is read out in a state in which the radiation R is not emitted after the accumulation period and image data is acquired is referred to as a "readout period".

Figure 6:
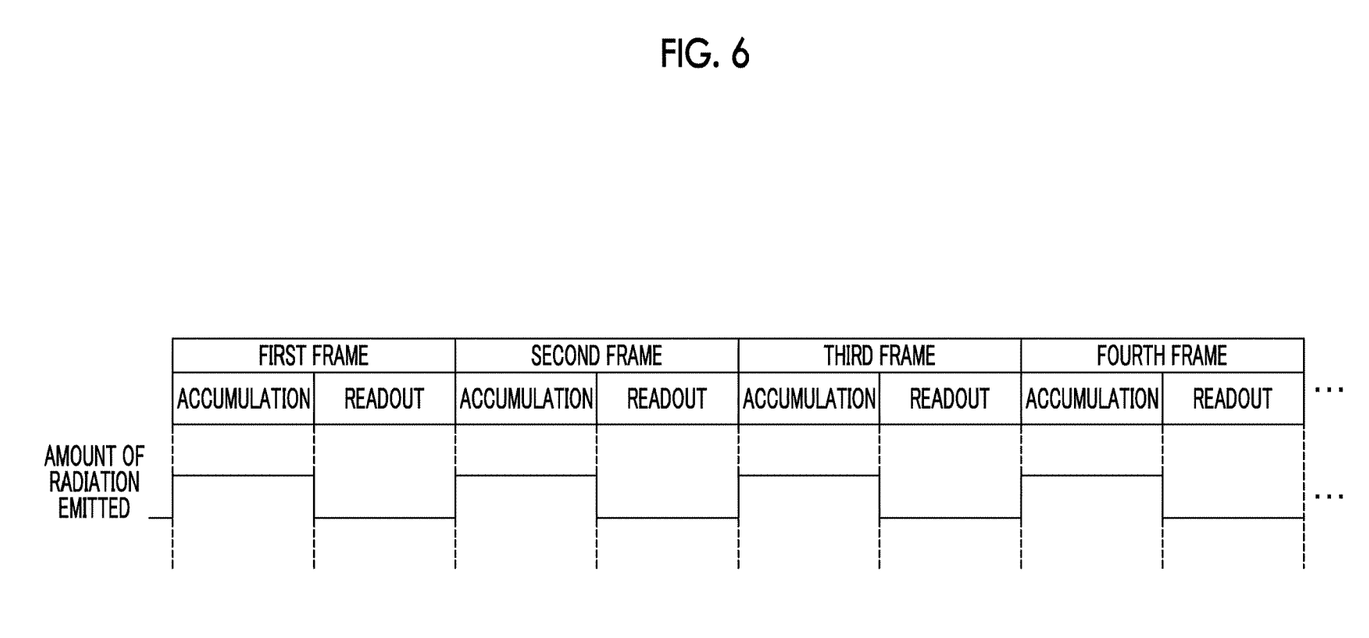
FIG. 6 is a timing chart illustrating fluoroscopy which is performed by emitting radiation in a pulse shape.

For example, as illustrated in FIG. 6, during fluoroscopy in a state in which the radiation R is emitted in a pulse shape, the accumulation period and the readout period are repeated according to a frame rate to perform fluoroscopy. A lower stage of FIG. 6 illustrates the amount of radiation per unit time.

The radiography system 10 according to this embodiment can perform imaging in a fast mode which is an example of a first imaging mode and imaging in a normal mode which is an example of a second imaging mode. First, an imaging process in the normal mode will be described with reference to FIG. 7.

Figure 7:
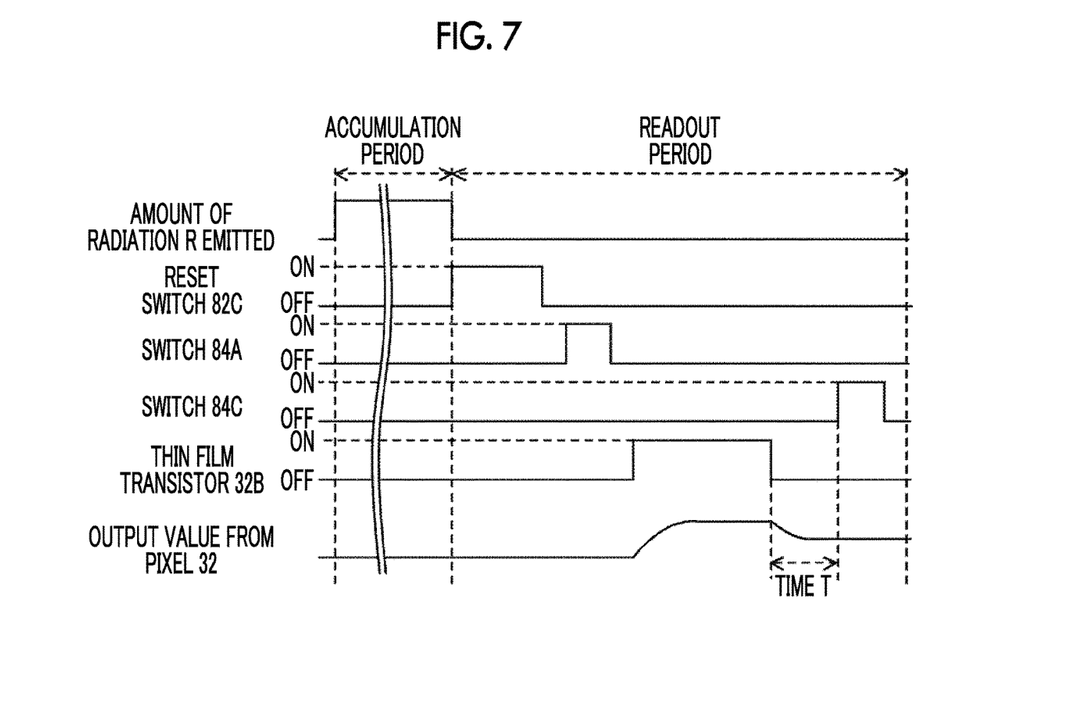
FIG. 7 is a timing chart illustrating an example of an accumulation process and a readout process in a normal mode.

As illustrated in FIG. 7, in the normal mode, for the readout period, first, the control unit 58 keeps the reset switch 82C on for a predetermined period to release the charge accumulated in the capacitor 82B. Then, the control unit 58 keeps the switch 84A on for a predetermined period such that the sample-and-hold circuit 83A samples and holds the electric signal output from the charge amplifier 82.

Then, the control unit 58 keeps the thin film transistor 32B on for a predetermined period. Then, the charge accumulated in the sensor unit 32A is transmitted as an electric signal to the data line 36. Then, the control unit 58 switches the thin film transistor 32B from the on state to an off state and then waits for a period T. Then, the control unit 58 keeps the switch 84C on for a predetermined period such that the sample-and-hold circuit 83B samples and holds the electric signal output from the charge amplifier 82. Then, the control unit 58 acquires, as an output value from the pixel 32, a digital signal which has been output from the operational amplifier 85 and converted by the A/D converter 88.

Figure 8:
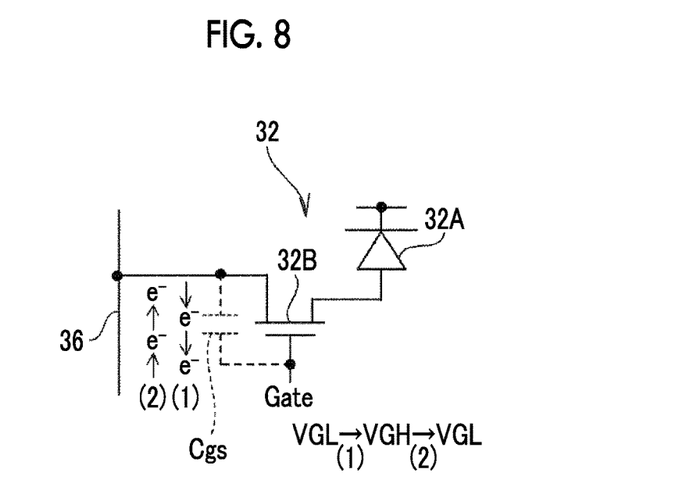
FIG. 8 is a circuit diagram illustrating a waiting period in the normal mode.

Next, the reason why the control unit 58 waits for the period T will be described with reference to FIG. 8. As illustrated in (1) of FIG. 8, when the thin film transistor 32B is changed from an off state to an on state, charge is moved from a parasitic capacitance Cgs between a gate electrode and a source electrode of the thin film transistor 32B. The charge generated by the movement is cancelled by charge which is generated from the parasitic capacitance Cgs when the thin film transistor 32B is changed from the on state to the off state, as illustrated in (2) of FIG. 8. For this reason, after changing the thin film transistor 32B from the on state to the off state, the control unit 58 waits for the period T to ensure the period until the charge is cancelled.

Next, the difference of an imaging process in the fast mode from the imaging process in the normal mode will be described with reference to FIG. 9.

Figure 9:
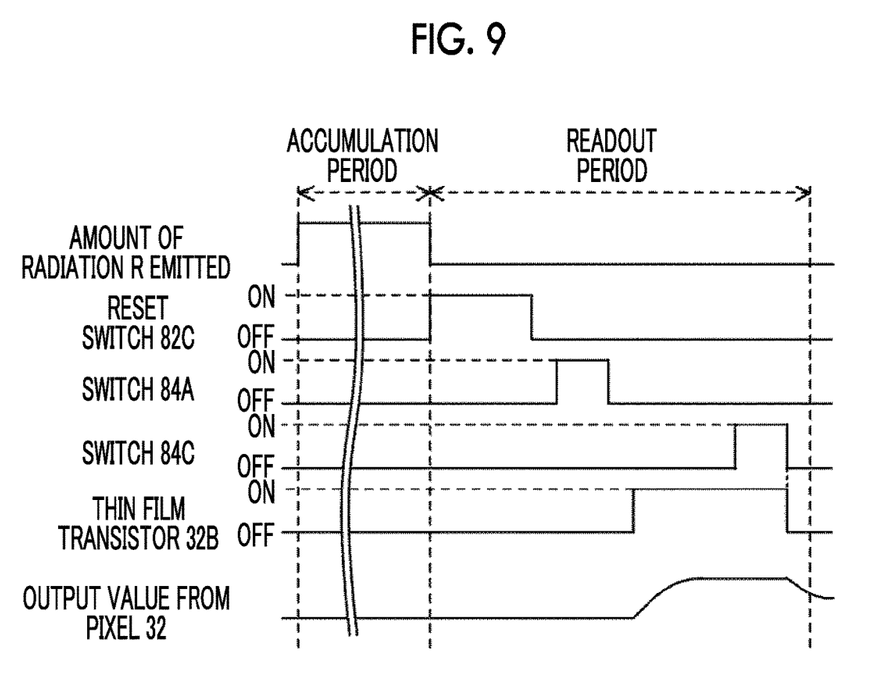
FIG. 9 is a timing chart illustrating an example of an accumulation process and a readout process in a fast mode.

As illustrated in FIG. 9, in the fast mode, for the readout period, the control unit 58 keeps the switch 84C on for a predetermined period while the thin film transistor 32B is in an on state. Then, the control unit 58 directs the sample-and-hold circuit 83B to sample and hold the electric signal output from the charge amplifier 82. Specifically, after turning on the thin film transistor 32B, the control unit 58 turns on the switch 84C to start a sampling operation of the sample-and-hold circuit 83B. Then, when turning off the thin film transistor 32B, the control unit 58 also turns off the switch 84C such that the sample-and-hold circuit 83B holds the level of the electric signal output from the charge amplifier 82.

That is, in the normal mode, the radiography apparatus 16 according to this embodiment turns off the thin film transistor 32B and samples and holds the electric signal transmitted through the data line 36 using the sample-and-hold circuit 83A. Then, after turning on the thin film transistor 32B, the radiography apparatus 16 turns off the thin film transistor 32B. After the period T elapses, the radiography apparatus 16 samples and holds the electric signal transmitted through the data line 36 using the sample-and-hold circuit 83B.

In contrast, in the fast mode, the radiography apparatus 16 according to this embodiment turns off the thin film transistor 32B and samples and holds the electric signal transmitted through the data line 36 using the sample-and-hold circuit 83A. Then, while the thin film transistor 32B is in an on state, the radiography apparatus 16 samples and holds the electric signal transmitted through the data line 36 using the sample-and-hold circuit 83B. Hereinafter, the electric signal sampled and held by the sample-and-hold circuit 83A is referred to as a "first electric signal" in order to avoid complication. In addition, hereinafter, the electric signal sampled and held by the sample-and-hold circuit 83B is referred to as a "second electric signal".

Therefore, in the fast mode, the charge generated from the parasitic capacitance Cgs when the thin film transistor 32B is changed from an on state to an off state is not cancelled. For this reason, the radiography apparatus 16 according to this embodiment performs the same control as that for the readout period in the fast mode when the radiation R is not emitted before a radiographic image is captured. Specifically, the radiography apparatus 16 performs the same control as that for the readout period in the fast mode in a state in which the radiation R is not emitted at the time when the radiography apparatus 16 is calibrated, such as during the setup of the radiography apparatus 16 and in a case in which a power switch is turned on first during the day. In addition, an example of the time when the radiography apparatus 16 is calibrated is a regular interval such as once an hour.

Then, the radiography apparatus 16 acquires, as a correction value, the digital signal obtained by converting the electric signal, which is the difference between the first electric signal and the second electric signal output from the operational amplifier 85 by the control when the radiation R is not emitted before a radiographic image is captured, using the A/D converter 88. The radiography apparatus 16 according to this embodiment acquires the correction value for each pixel 32.

In addition, the radiography apparatus 16 corrects the difference between the first electric signal and the second electric signal obtained by imaging in the fast mode, using the acquired correction value. Specifically, the radiography apparatus 16 subtracts the correction value acquired for each pixel from each pixel value of the image data which is indicated by the difference obtained by imaging in the fast mode to generate corrected image data.

For the readout period in the fast mode, the radiography apparatus 16 according to this embodiment inputs, to the thin film transistor 32B, a control signal with a voltage value equal to the voltage value of the control signal that is input to the thin film transistor 32B in a case in which the correction value is acquired. That is, in this embodiment, the value of a gate voltage that is input to the thin film transistor 32B in a case in which the correction value is acquired is equal to the value of a gate voltage that is input to the thin film transistor 32B in a case in which image data is acquired.

Here, the period for which a radiographic image is captured is the period from the input of a command to start imaging, such as a command to emit the radiation R which is input by the irradiation button, to the completion of the acquisition of image data indicating a radiographic image used for diagnosis. Specifically, for example, in a case in which the radiation emitting apparatus 12 emits the radiation R in a pulse shape while the irradiation button is being pressed and a still image is captured, the user, such as a radiology technician, presses the irradiation button in a case in which the user starts to take a radiographic image and keeps the irradiation button pressed. In this case, for example, the user visually checks that a still image obtained by imaging has been displayed on the display unit 98 of the console 18 and then stops pressing the irradiation button. That is, in this case, the period for which the irradiation button is being pressed is the period for which a radiographic image is captured.

For example, in a case in which the radiation emitting apparatus 12 emits the radiation R in a pulse shape while the irradiation button is being pressed and fluoroscopy is performed, the user presses the irradiation button in a case in which the user starts to take a radiographic image and keeps the irradiation button pressed. In this case, for example, the user visually checks that a motion picture obtained by imaging has been displayed on the display unit 98 of the console 18. Then, the user stops pressing the irradiation button in a case in which the motion picture displayed on the display unit 98 is determined to be a motion picture captured until the time required for diagnosis. That is, in this case, the period for which the irradiation button is being pressed is also the period for which a radiographic image is captured.

Figure 10:
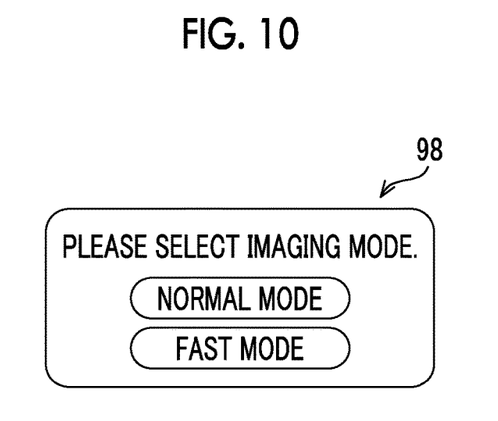
FIG. 10 is a diagram schematically illustrating an example of an imaging mode selection screen.

The radiography apparatus 16 according to this embodiment can be switched between imaging in the normal mode and imaging in the fast mode. In this embodiment, for example, the user selects the imaging mode through an imaging mode selection screen illustrated in FIG. 10. For example, in a case in which the user inputs an imaging menu through the console 18, the imaging mode selection screen is displayed on the display unit 98 and the user selects the imaging mode through the operation panel 100.

Next, the operation of the radiography system 10 according to this embodiment will be described with reference to FIGS. 11 and 12. Here, a case in which fluoroscopy is performed in a state in which the radiation R is emitted in a pulse shape will be described.

Figure 11:
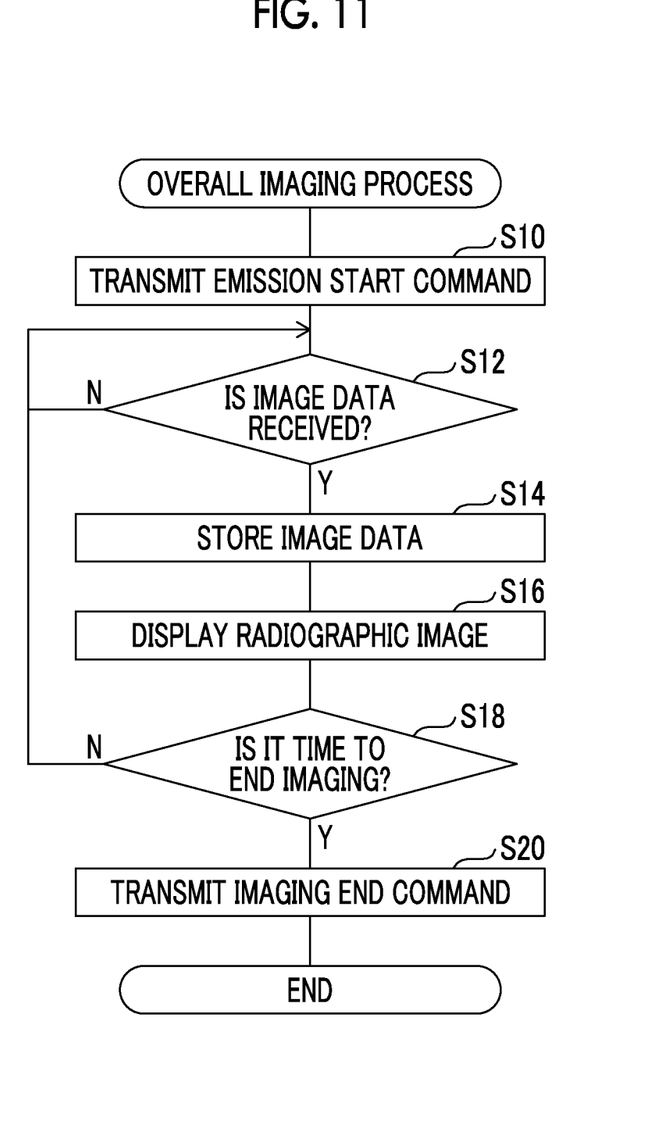
FIG. 11 is a flowchart illustrating the process flow of an overall imaging processing program according to the embodiment.

FIG. 11 is a flowchart illustrating the process flow of an overall imaging processing program which is executed by the CPU 90 of the console 18 in a case in which the user inputs an imaging menu including, for example, the name of the subject W, an imaging part, and imaging conditions through the operation panel 100. The overall imaging processing program is installed in the ROM 92 of the console 18 in advance. The imaging conditions include, for example, irradiation conditions, such as a tube voltage, a tube current, and a pulse irradiation period which are set to the radiation emitting apparatus 12, information indicating the imaging mode, and a frame rate.

Figure 12:
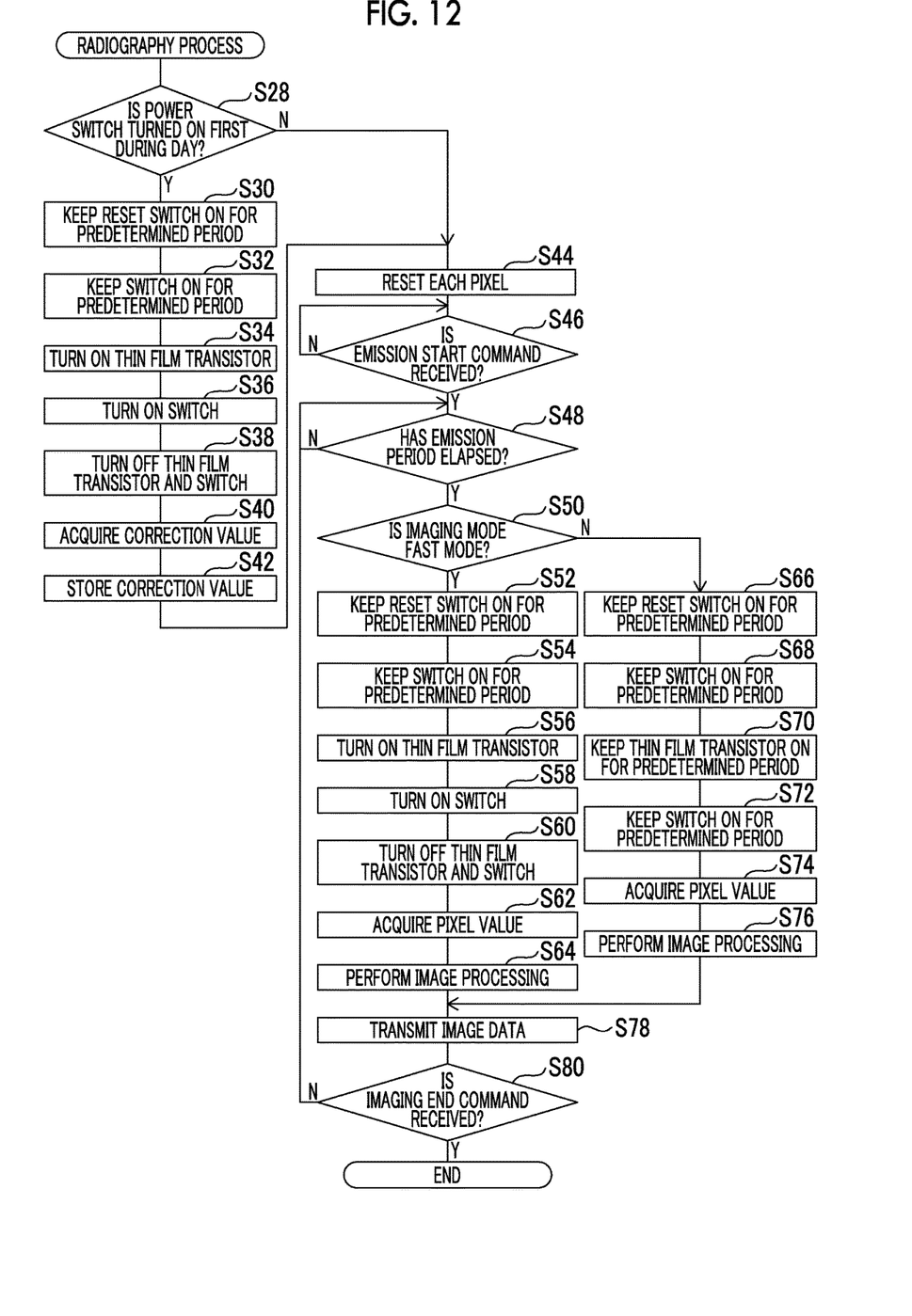
FIG. 12 is a flowchart illustrating the process flow of a radiography processing program according to the embodiment.

FIG. 12 is a flowchart illustrating the process flow of a radiography processing program that is executed by the control unit 58 of the radiography apparatus 16 in a case in which the power switch of the radiography apparatus 16 is in an on state. The radiography processing program is installed in a ROM of the memory 62 of the control unit 58 in advance.

In Step S10 of FIG. 11, the CPU 90 of the console 18 transmits information included in the input imaging menu to the radiography apparatus 16 through the communication unit 102 and transmits the emission conditions of the radiation R to the radiation emitting apparatus 12 through the communication unit 102. Then, the CPU 90 transmits a command to start the emission of the radiation R to the radiography apparatus 16 and the radiation emitting apparatus 12 through the communication unit 102. When receiving the emission conditions and the emission start command transmitted from the console 18, the radiation emitting apparatus 12 emits the radiation R in a pulse shape according to the received emission conditions. In a case in which the radiation emitting apparatus 12 includes an irradiation button, the radiation emitting apparatus 12 receives the emission conditions and the emission start command transmitted from the console 18. In a case in which the irradiation button is pressed, the radiation emitting apparatus 12 emits the radiation R in a pulse shape according to the received emission conditions.

Then, in Step S12, the CPU 90 waits until image data transmitted by the radiography apparatus 16 is received, which will be described below. In a case in which the CPU 90 receives the image data transmitted by the radiography apparatus 16, the determination result in Step S12 is "Yes" and the process proceeds to Step S14.

In Step S14, the CPU 90 stores the image data received in Step S12 in the storage unit 96. Then, in Step S16, the CPU 90 displays the radiographic image indicated by the image data received in Step S12 on the display unit 98.

Then, in Step S18, the CPU 90 determines whether it is time to end fluoroscopy. Example of the time when fluoroscopy ends include the time when a command to end fluoroscopy is input from the user through the operation panel 100 and the time when the irradiation button is pressed again. In a case in which the determination result in Step S18 is "No", the process returns to Step S12. In a case in which the determination result in Step S18 is "Yes", the process proceeds to Step S20.

In Step S20, the CPU 90 transmits a command to end fluoroscopy to the radiography apparatus 16 and the radiation emitting apparatus 12 through the communication unit 102 and then ends the overall imaging process. When receiving the command to end fluoroscopy transmitted from the console 18, the radiation emitting apparatus 12 ends the emission of the radiation R.

In Step S28 of FIG. 12, the control unit 58 of the radiography apparatus 16 determines whether the power switch has been turned on first during the day. In a case in which the determination result is "No", the process proceeds to Step S44. In a case in which the determination result is "Yes", the process proceeds to Step S30.

Then, in Steps S30 to S42, the control unit 58 performs the control for the readout period in the timing chart corresponding to the fast mode illustrated in FIG. 9 for the pixels 32 connected to each gate line 34 line by line. That is, in Step S30, the control unit 58 keeps the reset switch 82C of the charge amplifier 82 corresponding to each data line 36 on for a predetermined period. Then, in Step S32, the control unit 58 keeps the switch 84A of the sample-and-hold circuit 83A corresponding to each data line 36 on for a predetermined period. Then, in Step S34, the control unit 58 turns on the thin film transistor 32B.

Then, in Step S36, the control unit 58 turns on the switch 84C of the sample-and-hold circuit 83B corresponding to each data line 36. Then, in Step S38, the control unit 58 waits for a predetermined period, turns off the switch 84C of the sample-and-hold circuit 83B corresponding to each data line 36, and turns off the thin film transistor 32B.

Then, in Step S40, the control unit 58 acquires the digital signal input from the A/D converter 88 as the correction value. Then, in Step S42, the control unit 58 stores the correction value acquired in Step S40 in the storage unit 64 so as to be associated with the pixel 32 for which the correction value has been acquired.

Then, in Step S44, the control unit 58 performs a reset operation which extracts the charge accumulated in the sensor unit 32A of each pixel 32 in the radiation detector 20 and removes the charge. In addition, the control unit 58 may perform the reset operation in Step S44 only once, may repeat the reset operation a predetermined number of times, or may repeat the reset operation until the determination result in Step S46 which will be described below is "Yes".

Then, in Step S46, the control unit 58 waits until a command to start the emission of the radiation R is received. In a case in which the control unit 58 receives the emission start command transmitted from the console 18 in Step S10 of the overall imaging process through the communication unit 66, the determination result in Step S46 is "Yes" and the process proceeds to Step S48. In a case in which the radiation emitting apparatus 12 includes an irradiation button and the control unit 58 receives the emission start command transmitted from the console 18 and information indicating that the irradiation button has been pressed through the communication unit 66, the determination result in Step S46 is "Yes". In this case, for example, in a case in which the irradiation button has been pressed, the radiation emitting apparatus 12 may directly transmit information indicating that the irradiation button has been pressed to the radiography apparatus 16 or may transmit the information to the radiography apparatus 16 through the console 18.

In Step S48, the control unit 58 waits for the emission period of the radiation R which is included in the information transmitted from the console 18 in Step S10 of the overall imaging process. Then, in Step S50, the control unit 58 determines whether the selected imaging mode is the fast mode. In a case in which the determination result is "Yes", the process proceeds to Step S52.

In Steps S52 to S62, the control unit 58 performs the same process as that in Steps S30 to S40. Then, in Step S62, the control unit 58 acquires the value of each pixel 32 and stores image data formed by the acquired pixel values in the image memory 56. Then, in Step S64, the control unit 58 performs image processing including various types of correction for the image data stored in the image memory 56 in Step S62. In this embodiment, the control unit 58 performs offset correction for the image data stored in the image memory 56. Then, the control unit 58 performs a correction process which subtracts the correction value acquired for each pixel in Step S40 from the value of each pixel of the image data subjected to the offset correction for each corresponding pixel.

Then, the control unit 58 performs gain correction and defect pixel correction for the image data subjected to the correction process. The time when the correction process of subtracting the correction value is performed is not particularly limited. For example, the correction process of subtracting the correction value may be performed after the gain correction or may be performed after the defect pixel correction.

On the other hand, in a case in which the determination result in Step S50 is "No", the imaging mode is regarded as the normal mode and the process proceeds to Step S66.

In Steps S66 to S74, the control unit 58 performs the control for the readout period in the timing chart corresponding to the normal mode illustrated in FIG. 7 for the pixels 32 connected to each gate line 34 line by line. That is, in Step S66, the control unit 58 keeps the reset switch 82C of the charge amplifier 82 corresponding to each data line 36 on for a predetermined period, as in Step S30. Then, in Step S68, the control unit 58 keeps the switch 84A of the sample-and-hold circuit 83A corresponding to each data line 36 on for a predetermined period, as in Step S32.

Then, in Step S70, the control unit 58 keeps the thin film transistor 32B on for a predetermined period. At that time, the control unit 58 inputs a gate voltage with the same voltage value as the gate voltage input in Step S34 and Step S56 to the thin film transistor 32B to turn on the thin film transistor 32B.

Then, in Step S72, the control unit 58 waits for the period T and keeps the switch 84C of the sample-and-hold circuit 83B corresponding to each data line 36 on for a predetermined period. Then, in Step S74, the control unit 58 acquires the digital signal output from the A/D converter 88 as the pixel value. Then, the control unit 58 stores image data formed by the pixel values acquired for each pixel 32 in the image memory 56.

Then, in Step S76, the control unit 58 performs image processing including various types of correction for the image data stored in the image memory 56 in Step S74. In this embodiment, the control unit 58 performs offset correction for the image data stored in the image memory 56. Then, the control unit 58 performs gain correction and defect pixel correction for the image data subjected to the offset correction.

In Step S78, the control unit 58 transmits the image data subjected to the image processing in Step S64 or Step S76 according to the imaging mode to the console 18. Then, in Step S80, the control unit 58 determines whether the fluoroscopy end command transmitted from the console 18 in Step S20 of the overall imaging process has been received. In a case in which the determination result is "No", the process returns to Step S48. In a case in which the determination result is "Yes", the radiography process ends.

As described above, according to this embodiment, in a case in which the charge accumulated in the pixel 32 is read out, the thin film transistor 32B is turned off and the sample-and-hold circuit 83A samples and holds the first electric signal transmitted through the data line 36. In this case, the thin film transistor 32B is turned on and the sample-and-hold circuit 83B samples and holds the second electric signal transmitted through the data line 36. Therefore, it is possible to reduce the time required to capture a radiographic image.

In addition, according to this embodiment, the correction value is acquired before the change accumulated in the pixel 32 is read out. Therefore, it is possible to sequentially correct the pixels from which the readout of charge has been completed, using the correction value, even in a case in which the readout of the charge accumulated in all of the pixels 32 has not been completed.

Figure 13:
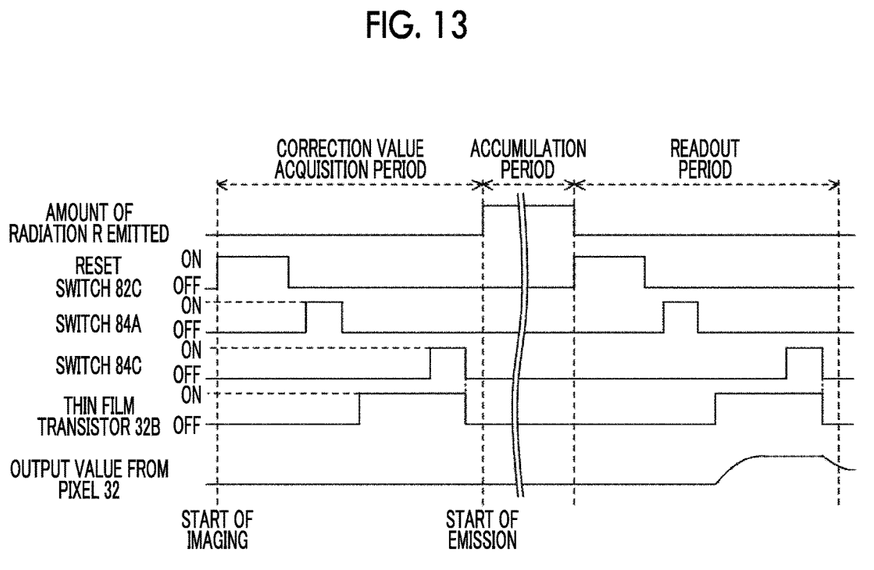
FIG. 13 is a timing chart illustrating an example of a correction value acquisition process, an accumulation process, and a readout process according to a modification example.

In the above-described embodiment, the case in which the correction value is acquired when the radiation R is not emitted before a radiographic image is captured has been described. However, the invention is not limited thereto. For example, the correction value may be acquired when the radiation R is not emitted each time a radiographic image is captured. In this case, for example, as illustrated in FIG. 13, in a case in which an imaging start command is input, control for acquiring the correction value may be performed. After the correction value is acquired, the emission of the radiation R may start. In this case, for example, in a case in which the user inputs an imaging menu, the console 18 transmits a command to start the acquisition of the correction value to the radiography apparatus 16. In a case in which the command to start the acquisition of the correction value is input, the radiography apparatus 16 acquire the correction value and transmits information indicating that the acquisition of the correction value has been completed to the console 18. Then, in a case in which the information indicating that the acquisition of the correction value has been completed is received, the console 18 performs the process after Step S10 of the overall imaging process. In this case, for example, the radiography apparatus 16 transmits the information indicating that the acquisition of the correction value has been completed to the console 18 and then performs the process after Step S44 of the radiography process.

In the above-described embodiment, the case in which the correction values are acquired for all of the pixels 32 has been described. For example, the correction values may be acquired for some predetermined pixels 32 and the acquired correction values may be used to correct the values of all of the pixels 32.

In the above-described embodiment, the case in which imaging is performed in the fast mode during fluoroscopy has been described. However, the invention is not limited thereto. For example, the same imaging operation in the fast mode as that in the above-described embodiment may be performed in a case in which a still image is captured.

In the above-described embodiment, the case in which the mode is switched between the normal mode and the fast mode according to the imaging mode selected by the user has been described. However, the invention is not limited thereto. For example, a radiographic image may be captured in the normal mode in a case in which a still image is captured and a radiographic image may be captured in the fast mode during fluoroscopy in a state in which the radiation R is emitted in a pulse shape. In addition, during fluoroscopy, a radiographic image may be captured in the normal mode in a case in which the frame rate is less than a predetermined value and a radiographic image may be captured in the fast mode during fluoroscopy in a state in which the frame rate is equal to or greater than the predetermined value.

In the above-described embodiment, the case in which an indirect-conversion-type radiation detector that converts the radiation R into light and converts the converted light into charge is applied to the radiation detector 20 has been described. However, the invention is not limited thereto. For example, a direct-conversion-type radiation detector that directly converts the radiation R into charge may be applied to the radiation detector 20.

In the above-described embodiment, the case in which the penetration side sampling radiation detector in which the radiation R is incident from the scintillator 22 is applied to the radiation detector 20 has been described. However, the invention is not limited thereto. For example, a so-called irradiation side sampling (ISS) radiation detector in which the radiation R is incident from the TFT substrate 30 may be applied to the radiation detector 20.

In the above-described embodiment, the functions implemented by the control unit 58 may be implemented by the CPU 90 of the console 18.

In the above-described embodiment, the aspect in which the overall imaging processing program is stored (installed) in the ROM 92 in advance has been described. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through a network.

In the above-described embodiment, the aspect in which the radiography processing program is stored in the ROM of the memory 62 of the control unit 58 in advance has been described. However, the invention is not limited thereto. The radiography processing program may be recorded in the above-mentioned recording medium and then provided. In addition, the radiography processing program may be downloaded from an external apparatus through the network.

EXPLANATION OF REFERENCES

10: radiography system
12: radiation emitting apparatus
14: radiation source
16: radiography apparatus
18: console
20: radiation detector
21: housing
22: scintillator
26: control substrate
28: case
30: TFT substrate
32: pixel
32A: sensor unit
32B: thin film transistor
34: gate line
36: data line
52: gate line driver
54: signal processing unit
56: image memory
58: control unit
60, 90: CPU
62: memory
64, 96: storage unit
66, 102: communication unit
70: power supply unit
82: charge amplifier
82A: operational amplifier
82B, 84B, 84D: capacitor
82C: reset switch
83A, 83B: sample-and-hold circuit
84A, 84C, 86A: switch
86: multiplexer
88: A/D converter
92: ROM
94: RAM
98: display unit
100: operation panel
104: bus
Cgs: parasitic capacitance
R: radiation
W: subject

What is claimed is:

1. A radiography apparatus comprising:
a radiation detector including a plurality of pixels, each of which includes a conversion element that generates a larger amount of charge as an amount of radiation emitted becomes larger and a switching element that is turned on and off according to a state of a control signal to read out charge generated by the conversion element, and which are two-dimensionally arranged, the radiation detector also including data lines which are connected to the pixels and through which the charge accumulated in the connected pixels is transmitted as an electric signal;
a first sample-and-hold unit and a second sample-and-hold unit that sample and hold the electric signal transmitted through the data line; and
a control unit that, in a case in which the charge accumulated in the pixels is read out, performs first control functions that cause the switching element to be turned off and the first sample-and-hold unit to sample and hold a first electric signal transmitted through the data line, and cause the switching element to be turned on and the second sample-and-hold unit to sample and hold a second electric signal transmitted through the data line,
wherein the control unit acquires, as a correction value, a difference between the first electric signal and the second electric signal which are obtained in advance by the control unit when the radiation is not emitted before a radiographic image is captured, and the control unit corrects the difference between the first electric signal and the second electric signal in a case in which the charge accumulated in the pixels is read out, using the correction value.

2. The radiography apparatus according to claim 1, wherein the control unit acquires, as a correction value, a difference between the first electric signal and the second electric signal which are obtained in advance by the control when the radiation is not emitted each time a radiographic image is captured and corrects the difference between the first electric signal and the second electric signal obtained by the control in a case in which the charge accumulated in the pixels is read out, using the correction value.

3. The radiography apparatus according to claim 2, wherein the control unit acquires the correction value before the radiation is emitted each time the radiographic image is captured.

4. The radiography apparatus according to claim 1, wherein the control unit acquires the correction value for each pixel and uses the correction value for the correction.

5. The radiography apparatus according to claim 1, wherein, in a case in which the charge accumulated in the pixel is read out, the control unit inputs, to the switching element, the control signal with a voltage value equal to a voltage value of the control signal which is input to the switching element in a case in which the correction value is acquired.

6. The radiography apparatus according to claim 1, wherein the control unit performs the control in a case in which the charge accumulated in the pixel is read out and in a case in which fluoroscopy is performed.

7. The radiography apparatus according to claim 6, wherein the fluoroscopy is fluoroscopy in a state in which the radiation is emitted in a pulse shape.

8. The radiography apparatus according to claim 1, wherein the apparatus is switchable between a first imaging mode in which the control unit performs the first control functions, and a second imaging mode in which the control unit turns off the switching element and directs the first sample-and-hold unit to sample and hold the first electric signal transmitted through the data line and the control unit turns on the switching element, turns off the switching element, and directs the second sample-and-hold unit to sample and hold the second electric signal transmitted through the data line.

9. The radiography apparatus according to claim 1, wherein the switching element includes amorphous silicon.

10. The radiography apparatus according to claim 1, wherein:
the switching element has a gate electrode and a source electrode, and the correction value corresponds to currents generated by a parasitic capacitance between the gate electrode and the source electrode of the switching element, in a case in which the switching element is changed from an on state to an off state.

11. A radiography method that is performed by a radiography apparatus comprising a radiation detector including a plurality of pixels, each of which includes a conversion element that generates a larger amount of charge as an amount of radiation emitted becomes larger and a switching element that is turned on and off according to a state of a control signal to read out charge generated by the conversion element and which are two-dimensionally arranged, and data lines which are connected to the pixels and through which the charge accumulated in the connected pixels is transmitted as an electric signal and a first sample-and-hold unit and a second sample-and-hold unit that sample and hold the electric signal transmitted through the data line, the method comprising:

in a case in which the charge accumulated in the pixels is read out, sampling and holding a first electric signal transmitted through the data line by the first sample-and-hold unit while turning off the switching element, sampling and holding a second electric signal transmitted through the data line by the second sample-and-hold unit while turning off the switching element, acquiring, as a correction value, a difference between the first electric signal and the second electric signal, which are obtained in advance when the radiation is not emitted before a radiographic image is captured, and correcting the difference between the first electric signal and the second electric signal in a case in which the charge accumulated in the pixels is read out, using the correction value.

12. A non-transitory computer readable medium storing a program that causes a computer to execute a process to control a radiography apparatus, the apparatus comprising a radiation detector including a plurality of pixels, each of which includes a conversion element that generates a larger amount of charge as an amount of radiation emitted becomes larger and a switching element that is turned on and off according to a state of a control signal to read out charge generated by the conversion element and which are two-dimensionally arranged, and data lines which are connected to the pixels and through which the charge accumulated in the connected pixels is transmitted as an electric signal and a first sample-and-hold unit and a second sample-and-hold unit that sample and hold the electric signal transmitted through the data line, the process comprising:

in a case in which the charge accumulated in the pixels is read out, sampling and holding a first electric signal transmitted through the data line by the first sample-and-hold unit while turning off the switching element, sampling and holding a second electric signal transmitted through the data line by the second sample-and-hold unit while turning off the switching element, acquiring, as a correction value, a difference between the first electric signal and the second electric signal, which are obtained in advance when the radiation is not emitted before a radiographic image is captured, and correcting the difference between the first electric signal and the second electric signal in a case in which the charge accumulated in the pixels is read out, using the correction value.

\* \* \* \* \*

UNITED STATES PATENT AND TRADEMARK OFFICE
CERTIFICATE OF CORRECTION

PATENT NO. : 10,274,618 B2
APPLICATION NO. : 15/792775
DATED : April 30, 2019
INVENTOR(S) : Kenji Nakamura It is certified that error appears in the above-identified patent and that said Letters Patent is hereby corrected as shown below:

In the Claims

Column 16, Claim 2, Lines 5 and 8, recite the term "control". This term should read "control unit".

Signed and Sealed this
Thirtieth Day of July, 2019

Andrei Iancu
*Director of the United States Patent and Trademark Office*